(12) United States Patent
Potter

(10) Patent No.: US 12,013,669 B1
(45) Date of Patent: Jun. 18, 2024

(54) SYSTEM FOR A PROXIMITY SENSING WRISTWATCH DEVICE

(71) Applicant: Shannon J. Potter, Hobe Sound, FL (US)

(72) Inventor: Shannon J. Potter, Hobe Sound, FL (US)

(*) Notice: Subject to any disclaimer, the term of this patent is extended or adjusted under 35 U.S.C. 154(b) by 484 days.

(21) Appl. No.: 17/198,459

(22) Filed: Mar. 11, 2021

(51) Int. Cl.
| | |
|---|---|
| *G04G 21/08* | (2010.01) |
| *A61B 5/00* | (2006.01) |
| *A61B 5/024* | (2006.01) |
| *G01K 1/024* | (2021.01) |
| *G01K 1/24* | (2006.01) |
| *G01K 13/20* | (2021.01) |
| *G04G 9/00* | (2006.01) |
| *G04G 21/02* | (2010.01) |
| *G06F 3/041* | (2006.01) |
| *G16H 50/80* | (2018.01) |

(52) U.S. Cl.
CPC ........... *G04G 21/08* (2013.01); *A61B 5/0006* (2013.01); *A61B 5/0008* (2013.01); *A61B 5/024* (2013.01); *A61B 5/681* (2013.01); *A61B 5/6824* (2013.01); *G01K 1/024* (2013.01); *G01K 1/24* (2013.01); *G01K 13/20* (2021.01); *G01K 13/223* (2021.01); *G04G 9/0064* (2013.01); *G04G 21/02* (2013.01); *G04G 21/025* (2013.01); *G06F 3/0412* (2013.01); *G16H 50/80* (2018.01)

(58) Field of Classification Search
CPC ...... G04G 21/08; G04G 21/02; G04G 21/025; G04G 9/0064; G01K 13/20; G01K 13/223; G01K 1/024; G01K 1/24; A61B 5/0006; A61B 5/0008; A61B 5/024; A61B 5/681; A61B 5/6824; G06F 3/0412; G16H 50/80
See application file for complete search history.

(56) References Cited

U.S. PATENT DOCUMENTS

| | | | | |
|---|---|---|---|---|
| D322,762 | S  * | 12/1991 | Muller | G04B 47/065 |
| | | | | D10/32 |
| 9,251,686 | B1 | 2/2016 | Reich | |
| 10,401,800 | B2 | 9/2019 | Cardinali | |
| 2015/0099941 | A1* | 4/2015 | Tran | A61B 5/1112 |
| | | | | 600/300 |
| 2018/0000418 | A1* | 1/2018 | Li | A61B 5/6844 |
| 2020/0257249 | A1* | 8/2020 | Nozawa | G04B 47/065 |
| 2020/0272105 | A1* | 8/2020 | Hirayama | G04B 37/08 |
| 2020/0323437 | A1* | 10/2020 | Lee | A61B 5/14551 |
| 2020/0393797 | A1* | 12/2020 | Hu | G04B 37/1486 |
| 2022/0045554 | A1* | 2/2022 | Leabman | H02J 50/80 |

* cited by examiner

*Primary Examiner* — Edwin A. Leon
*Assistant Examiner* — Sean R Brannon
(74) *Attorney, Agent, or Firm* — Sanchelima & Associates, P.A.; Christian Sanchelima; Jesus Sanchelima

(57) ABSTRACT

A wristwatch device includes a smartwatch having a digital display screen. The watch device also includes biometric sensors and proximity sensors. Furthermore, the watch device is configured to determine the proximity of a person to the watch wearer and display an indication that corresponds to that person's body temperature. Additionally, the wristwatch device may also serve as a panic button which will alert a user when their vital signs and temperature changes rapidly. The system will record a user's vitals and temperatures every hour. In the event of a panic situation, the system will automatically screenshot and record the user's latest temperature and vitals. This information will may be linked to other individuals such as family members.

2 Claims, 4 Drawing Sheets

SYSTEM FOR A PROXIMITY SENSING WRISTWATCH DEVICE

BACKGROUND OF THE INVENTION

1. Field of the Invention

The present invention relates to a wristwatch device and, more particularly, to a proximity sensing wristwatch device that includes biometric sensors and proximity sensors for determining the proximity of a person and indicating that persons temperature on a display screen.

2. Description of the Related Art

Several designs for a wristwatch device have been designed in the past. None of them, however, include a wristwatch device comprising a smartwatch having a digital display screen. The watch device also includes biometric sensors and proximity sensors. Furthermore, the watch device is configured to determine the proximity of a person to the watch wearer and display an indication that corresponds to that person's body temperature. Additionally, the wristwatch device may also serve as a panic button which will alert a user when their vital signs and temperature changes rapidly. The system will record a user's vitals and temperatures every hour. In the event of a panic situation, the system will automatically screenshot and record the user's latest temperature and vitals. This information will may be linked to other individuals such as family members. It is known that to avoid getting sick, there is a need to be cautious of one's proximity to other individuals. Therefore, there is a need for a wristwatch device for alerting the proximity and temperature of nearby individuals.

Applicant believes that a related reference corresponds to U.S. Pat. No. 10,401,800 issued for a wrist worn device that includes a temperature sensor and a proximity sensor. Applicant believes that another related reference corresponds to U.S. Pat. No. 9,251,686 issued for a wearable device that includes a sensing system which provides location data and ambient temperature data to a second device. However, the cited references differ from the present invention because they fail to disclose a wristwatch device comprising a smartwatch having a digital display screen, wherein the watch device includes biometric sensors and proximity sensors. The watch device is configured to determine the proximity of a person to the watch wearer and display an indication that corresponds to that person's body temperature.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a system for a proximity sensing wristwatch device which provides peace of minds to family and loved ones by keeping them constantly informed of a user's temperature and vital signs.

It is another object of this invention to provide a system for a proximity sensing wristwatch device which aids a user from coining into contact with viruses that may be transmitted by maintaining a close proximity to other individuals.

It is still another object of the present invention to provide a system for a proximity sensing wristwatch device which also serves as a panic button that records a user's vitals and temperature to better inform loved ones and first responders.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
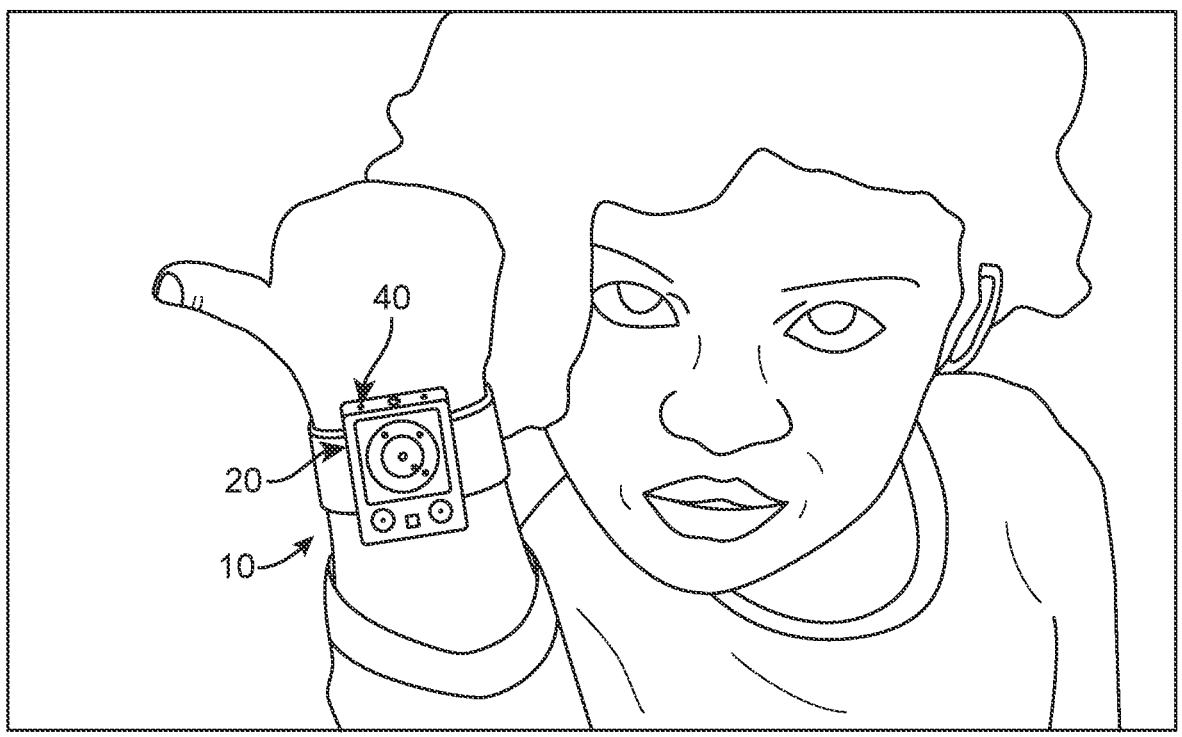
FIG. 1 represents an operational isometric view of a proximity sensing wristwatch device 10 in accordance with an embodiment of the present invention.

Referring now to the drawings, where the present invention is generally referred to with numeral 10, it can be observed a system for a proximity sensing wristwatch device 10 which basically includes a device assembly 20 and a sensor assembly 40.

Device assembly 20 includes a device 22 as observed in the drawings. In on embodiment, device 22 is an interactive electronic device having a rectangular wristwatch shape. It should be understood that other shapes may be implemented for device 22 and it is not limited to being rectangular in shape. Further, device 22 includes a display screen 23 which is embedded onto the top surface of the device. In one embodiment, display screen 23 is of an interactive variety. Display screen 23 may be provided as a touch screen LED display. Other embodiments may feature an LED display that is not of the touch screen variety in which the device 22 is interacted with buttons provided on the device. Device 22 may also include adjustment buttons 24 which are used to modify various interactive parameters that are implemented into the device. These parameters will be described thoroughly throughout the present specification. In one implementation, adjustment buttons 24 are circular pressable buttons located directly beneath the display screen 23. In another implementation, adjustments buttons 24 are soft touch buttons which are pressure sensitive to a user's interactions thereon.

Device assembly 20 further includes a speaker 25 which is implemented onto device 22 as observed in the drawings. In one embodiment, speaker 25 is implemented along a top sidewall of the device 25. Speaker 25 is provided as to alert a user of various conditions that are detected by the device 22. In one implementation, speaker 25 broadcasts an audible repeating alert in the event that an emergency occurs or a condition is met by device 22. Further, device 22 includes strap slots 26 along the lateral sides thereof. In one embodiment, strap slots 26 partially extend within the body of device 22 in order to mountable receive the strap 27 therein. Other embodiments may feature a slot 26 which extends entirely through device 22 in order to receive the strap 27. In the present embodiment, strap 27 is an interchangeable strap. As such straps 27 may be provided as being made of a different material to provide a customizable fashionable device. Strap 27 could be made of a metal material, gold, silver, stainless steel, or variations of cloth material.

Figure 2:
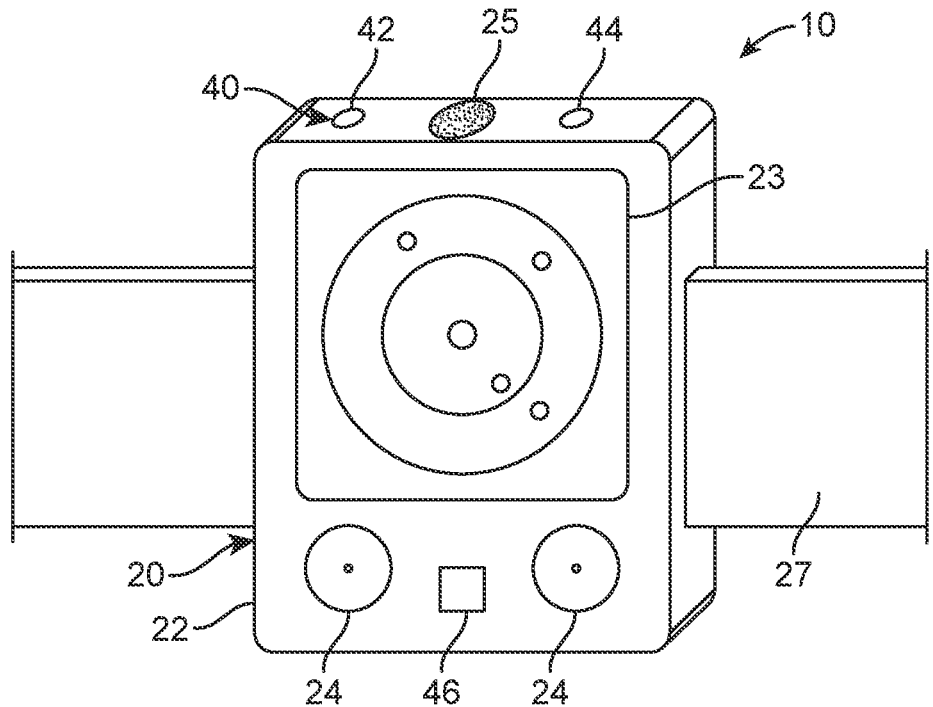
FIG. 2 shows an enlarged isometric view of proximity sensing wristwatch device 10 depicting a device assembly 20 and a sensor assembly 40, wherein the device assembly 20 is displaying a temperature and location of individuals in a given proximity.
Figure 3:
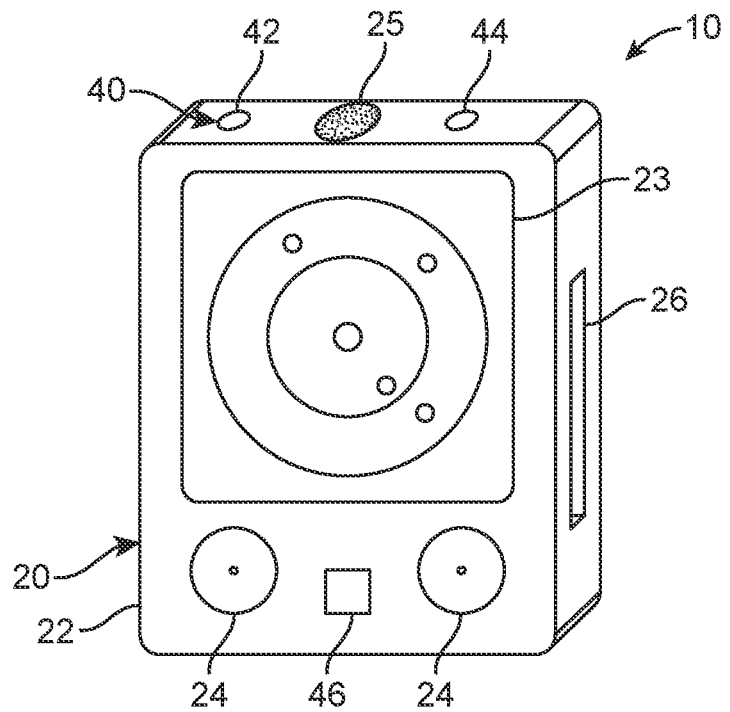
FIG. 3 illustrates another enlarged isometric view of proximity sensing wristwatch device 10 depicting device assembly 20 and sensor assembly 40, wherein the device assembly 20 is displaying the temperature and vitals of a given user.
Figure 4:
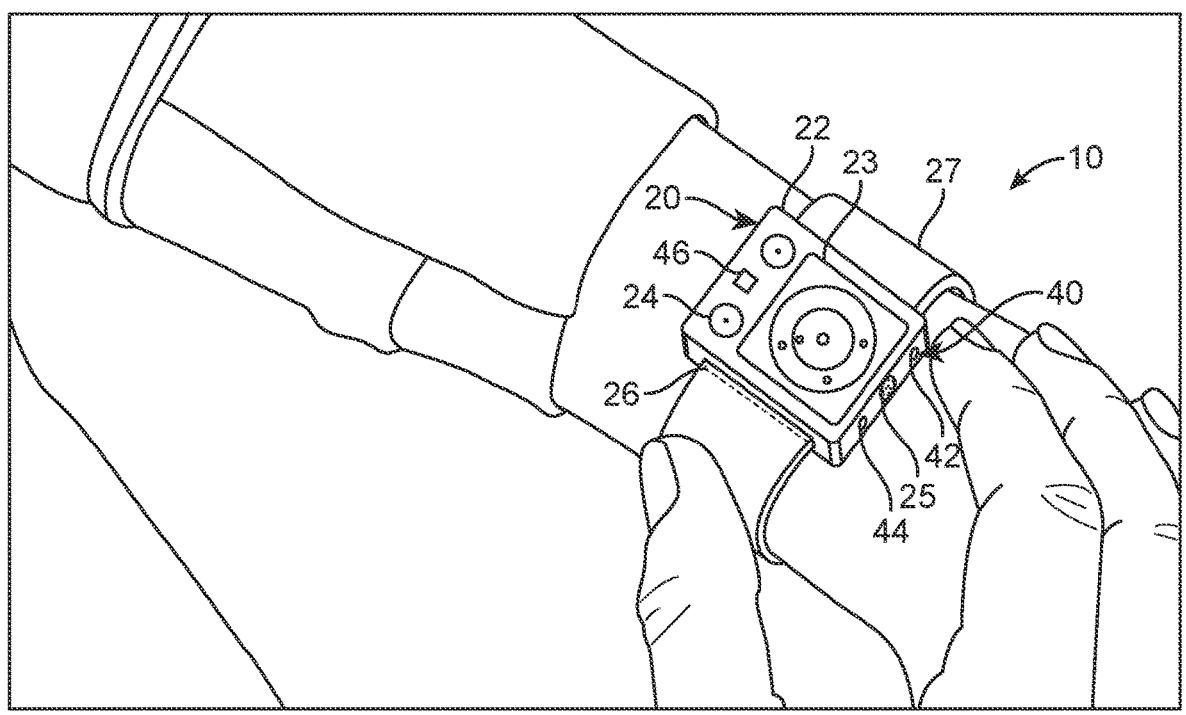
FIG. 4 is a representation of an enlarged isometric view of proximity sensing wristwatch device 10 being mounted onto the wrist of a user in accordance with an embodiment of the present invention.
Figure 5:
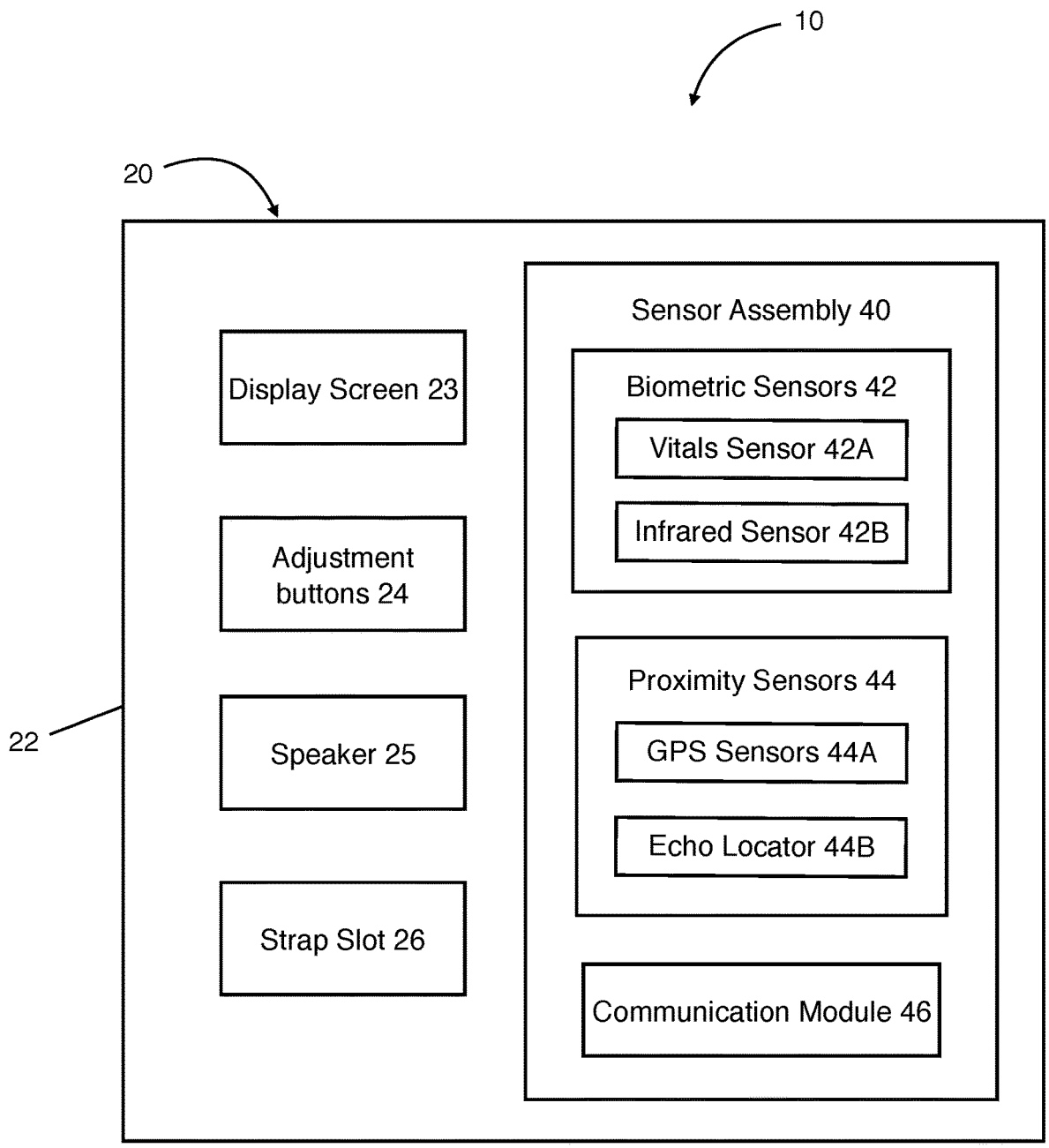
FIG. 5 depicts the sensors such as the biometric sensors 42 and the proximity sensors 44 of the sensor assembly 40 that are disposed within the device assembly 20.

Sensor assembly 40 includes biometric sensors 42 and proximity sensors 44 which are communicably implemented into device 22. In one embodiment, biometric sensors 42 include a vital sensor 42A and an infrared sensor 42B. Vitals sensor 42A may be provided as a sensor which records the body temperature of a wearer and further monitors and records the heartrate of a wearer. In one embodiment, the wearer is an elderly individual who lives alone. Vital sensor 42A will then record the vital signs of the wearer every hour and record the information within device 22. In one embodiment, one of adjustment buttons 24 may be configured to be a panic button, that when engaged by a user, will record and screen shot the last known temperature and vitals which were measured by the device 22. This will provide first responders with an accurate understanding of the body readings of a user when they were in distress in order to provide the appropriate care. Further, as observed in FIG. 3, the vital signs and temperature signs of a user may be placed on display for the wearer to monitor. In one embodiment, vital sensor 42A also records blood pressure vitals of a user and then reminds a user via an audible alert to take their medicine for their blood pressure. In one embodiment, infrared sensor 42B detects the temperature of other individuals in a surrounding predetermined area. In the present embodiment, this predetermined area may be provided as 6 feet or 10 feet. Infrared sensor 42B will detect the temperatures of individuals who come into a 6 feet or 10 feet radius of the wearer and then display those temperatures on display screen 23 as observed in FIG. 2 of the drawings. Due to rising concerns of Covid-19, this will allow users to monitor the temperature of individuals which come near a user in order to provide peace of mind. In one embodiment, device 22 will provide an audible alert when infrared sensor detects an individual within the given radius which has a temperature which reads above 100 degrees. Further adjustment buttons 24 may be used in order to modify the radius of infrared sensor 42B. As such a user may customize their preferred radius depending on their known surroundings. Display screen 23 may display the recorded temperatures using colors wherein red represents a high temperature that is not safe (above 100 degrees).

In one embodiment, proximity sensors 44 includes a GPS sensor 44A and an echo locater sensor 44B. GPS sensor 44A may be provided as a global positioning satellite module which records a user's coordinates at any time. In one embodiment, the GPS coordinates of a wearer are recorded every hour correspondingly to the time in which the vital signs and temperature signs of the wearer are also recorded. This information may also be made available to loved ones and first responders to aid in providing appropriate care to the wearer if need be. In one implementation, a child will engage a panic button when they may see strangers and feels an threat. The device 22 will then broadcast their GPS coordinates and vitals to immediate family and first responders to locate the child. Echo locator 44B is implemented to determine the location of other individuals around a predetermined area of the device 22. In the present implementation, this predetermined area corresponds to the 6 feet or 10 feet radius that is implemented for the infrared sensor 42B. Echo locator sensor 44B and infrared sensor 42B work in tandem in order to locate the distance of an individual within the predetermined area and also read their temperature. This allows a wearer to better adhere to social distancing guidelines to prevent the spread of Covid-19 as observed in FIG. 2. In the present implementation, device 22 broadcasts an audible alert whenever an individual comes within the predetermined area set for the sensors. Sensor assembly 40 further includes a communication module 46 enabling the device to be communicably connected to other devices through various means of communication. This may include communication means such as WiFi, Bluetooth, LTE, 4G, 5G, and other means.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a proximity sensing wristwatch device, comprising:
   a) a device assembly including a smartwatch device having a touch screen LED digital display screen, said device assembly further including strap slots along lateral side ends thereof, said smartwatch device further including adjustments buttons in the form as pressure sensitive buttons which are located beneath said touch screen LED digital display screen, said smartwatch device further including a speaker located on a top sidewall thereof, wherein said strap slots receive a strap therein; and
   b) a sensor assembly including biometric sensors, proximity sensors, and a communication module;
   i) wherein said biometric sensors include a vitals sensor and an infrared sensor, wherein said infrared sensor detects and displays temperature data of people within a 6 foot radius of said smartwatch device, wherein said vitals sensors records a temperature and a heart rate of a wearer every hour; and
   ii) wherein said proximity sensors include a GPS sensor and an echo locator, wherein said echo locator detects and displays the location of people within a 6 foot radius of said smartwatch device, wherein said GPS sensor records GPS coordinates of said smartwatch device every hour.

2. A system for a proximity sensing wristwatch device, consisting of:
   a) a device assembly including a smartwatch device having a touch screen LED digital display screen, said device assembly further including strap slots along lateral side ends thereof, said smartwatch device further including adjustments buttons in the form as pressure sensitive buttons which are located beneath said touch screen LED digital display screen, said smartwatch device further including a speaker located on a top sidewall thereof, wherein said strap slots receive a strap therein, wherein said strap slots extend partially within said smartwatch device; and b) a sensor assembly, including:

i) biometric sensors consisting of a vitals sensor and an infrared sensor, wherein said vitals sensor records and measures a heart rate, a temperature, and a blood pressure of a wearer every hour, wherein said infrared sensor detects individuals within a 6 foot radius of the smartwatch device and displays a temperature detected on the touch screen LED display screen;

ii) proximity sensors consisting of a GPS sensor and an echolocator, wherein said GPS sensor records a GPS coordinate of the smartwatch device in tandem with said vitals sensor, wherein said echo locator detects and displays a location of individuals within a 6 foot radius on the touch screen digital display screen; and iii) a communication module to transmit data collected from said sensor assembly to external devices.

\* \* \* \* \*